(12) United States Patent
Alshehri et al.

(10) Patent No.: US 12,329,404 B1
(45) Date of Patent: Jun. 17, 2025

(54) CHALAZION CLAMP

(71) Applicant: KING SAUD UNIVERSITY, Riyadh (SA)

(72) Inventors: Mohammed Abdullah Alshehri, Riyadh (SA); Hamad Nasser Albageah, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/074,731

(22) Filed: Mar. 10, 2025

(51) Int. Cl.
*A61B 17/30* (2006.01)
*A61B 90/35* (2016.01)
*A61B 17/00* (2006.01)

(52) U.S. Cl.
CPC .............. *A61B 17/30* (2013.01); *A61B 90/35* (2016.02); *A61B 2017/00747* (2013.01)

(58) Field of Classification Search
CPC ... A61B 17/30; A61B 17/28; A61B 2017/301; A61B 2017/303; A61B 2017/305; B25B 9/02; A47J 43/283; A45D 26/0066
See application file for complete search history.

(56) References Cited

U.S. PATENT DOCUMENTS

| | | | |
|---|---|---|---|
| 3,392,727 A * | 7/1968 | Hanlon | A61B 17/30 294/99.2 |
| 6,988,814 B1 | 1/2006 | Correa | |
| 10,188,239 B2 | 1/2019 | Knittig et al. | |
| 10,281,136 B2 | 5/2019 | Zadro et al. | |
| 2011/0140639 A1 | 6/2011 | Shih | |
| 2016/0262931 A1 | 9/2016 | Bhattacharjee | |

FOREIGN PATENT DOCUMENTS

| | | |
|---|---|---|
| CN | 216602958 U | 5/2022 |
| CN | 219763732 U | 9/2023 |

\* cited by examiner

*Primary Examiner* — Majid Jamialahmadi
(74) *Attorney, Agent, or Firm* — Nath, Goldberg & Meyer; Joshua B. Goldberg

(57) ABSTRACT

A chalazion clamp includes a main clamp body having a first jaw member and a second jaw member connected together at first ends thereof so that opposing second ends thereof are biased into an open configuration. A threaded fastener extends through the first jaw member and abuts the second jaw member. The second ends of the first and second jaw members can be moved towards each other to a second closed position or a "gripping" configuration upon simultaneous application of pressure to the first and second jaw members. In the gripping configuration, the second ends of the first and second jaw members are biased towards each other to capture tissues therebetween during surgical procedures, such as lip biopsies. The threaded fastener can be adjusted to maintain the first and second jaw members in the desired gripping configuration.

16 Claims, 3 Drawing Sheets

CHALAZION CLAMP

BACKGROUND

1. Field

The present disclosure relates to a chalazion clamp and, particularly, to a chalazion clamp configured to provide illumination, tissue stabilization, and adjustable pressure.

2. Description of the Related Art

Chalazion clamps are essential tools in oral surgical procedures, particularly for lip biopsies, where they are used to clamp and retract soft tissues to facilitate access and visibility. Traditional chalazion clamps typically consist of a simple pair of forceps-like arms with limited functionality. They lack features for adjustable pressure control, integrated lighting, or effective tissue stabilization.

In delicate oral procedures, clear visibility of the target tissue is crucial. Stable tissue positioning is necessary to prevent unwanted movement that could complicate the procedure. Additionally, precise control of applied pressure is essential to securely hold the tissue without causing unnecessary trauma. Furthermore, the ability to thoroughly sterilize all components of surgical instruments is paramount in maintaining proper hygiene and preventing infections.

Conventional chalazion clamps frequently fall short in addressing these needs comprehensively. They often lack mechanisms for fine-tuning applied pressure and illumination, and have limited tissue stabilization capabilities. Moreover, conventional clamps with fixed lighting components can be challenging to sterilize effectively.

Thus, a chalazion clamp solving the afore-mentioned problems is desired.

SUMMARY

The present subject matter relates to a chalazion clamp for use during surgical procedures, such as oral biopsies. The chalazion clamp incorporates a detachable light source, tissue stabilization features, and an adjustable pressure mechanism. The chalazion clamp provides enhanced visibility and control compared to conventional clamping devices used for oral surgeries and biopsies.

The chalazion clamp includes a first jaw member and a second jaw member connected together at first ends thereof so that opposing second ends thereof are biased into an open configuration. The second ends of the first and second jaw members can be moved towards each other to a second closed position or a "gripping" configuration upon simultaneous application of pressure to the first and second jaw members. In the gripping configuration, the second ends of the first and second jaw members are biased towards each other to capture tissues therebetween during surgical procedures, such as lip biopsies.

According to an embodiment, the chalazion clamp includes a main clamp body including a first jaw member and a second jaw member connected together at first ends thereof and spaced apart at second ends thereof, the second end of the first jaw member having a circular wall, a plurality of gripping teeth protruding from an inner surface of the circular wall, and a central opening defined through the circular wall, and the second end of the second jaw member including a plate, and a threaded fastener extending through the first jaw member and abutting the second jaw member, the threaded fastener including a threaded shaft extending through the first jaw member and a knob connected to the shaft at a first end; and a light source housing including a light source, the light source housing detachably connected to the plate.

According to an embodiment, the chalazion clamp includes a main clamp body including a first jaw member and a second jaw member connected together at first ends thereof and spaced apart at second ends thereof, the second end of the first jaw member having a circular wall, a plurality of gripping teeth protruding from an inner surface of the circular wall, and a central opening defined through the circular wall, and the second end of the second jaw member including a plate, a threaded fastener extending through the first jaw member and abutting the second jaw member, the threaded fastener including a threaded shaft extending through the first jaw member and a knob connected to the shaft at a first end, and an incremental position adjuster connected to the first and second jaw members, the incremental position adjuster including a bar extending from one of the first and second jaw members and a pin extending from another one of the first and second jaw members, the bar including a plurality of holes defined therethrough and configured to releasably engage the pin within any of the plurality of holes; and a light source housing including a light source, the light source housing detachably connected to the plate.

These and other features of the present subject matter will become readily apparent upon further review of the following specification.

DETAILED DESCRIPTION OF THE PREFERRED EMBODIMENTS

Figure 1:
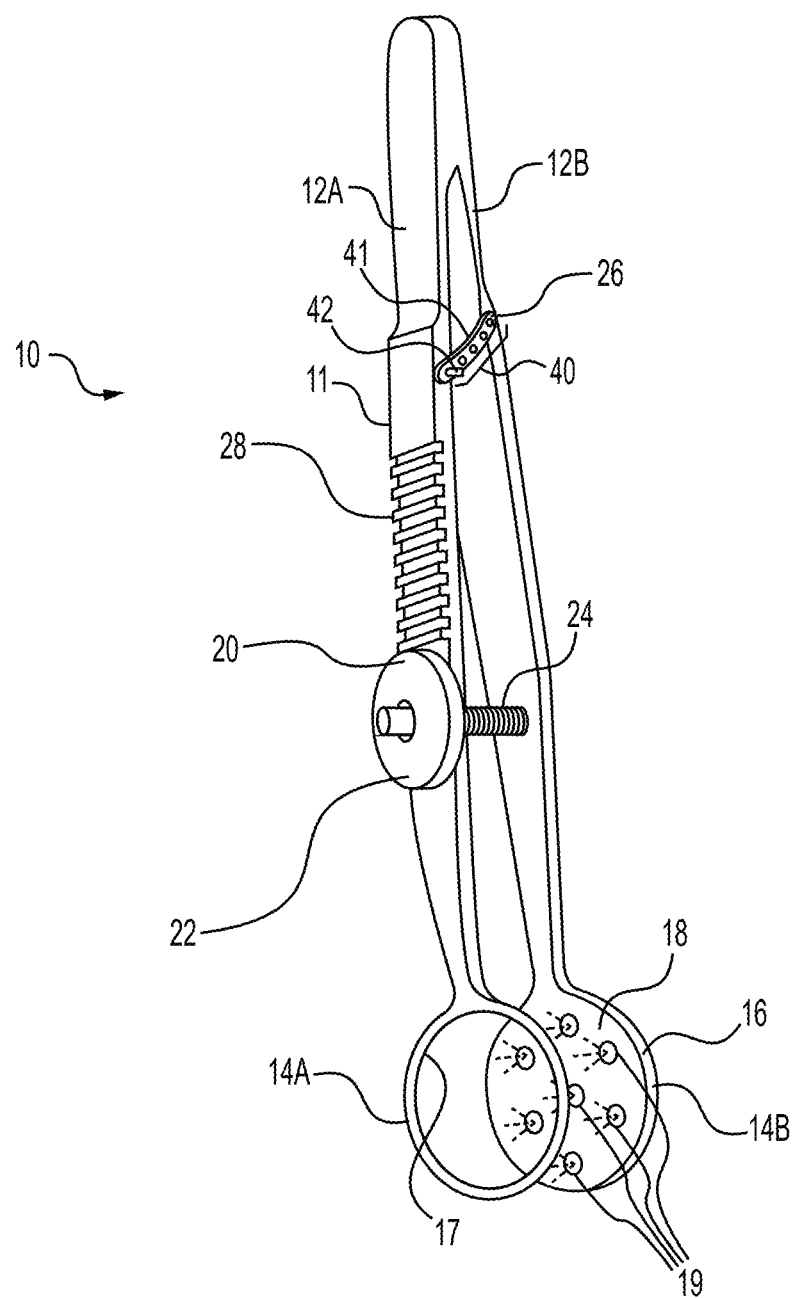
FIG. 1 is a perspective view of the chalazion clamp according to the present teachings.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

According to an embodiment, the present subject matter relates to a chalazion clamp 10 including a main clamp body 11 having a first jaw member 12a and a second jaw member 12b connected together at first ends thereof so that opposing second ends 14a, 14b thereof are biased into an open configuration. The second ends 14a, 14b of the first and second jaw members 12a, 12b can be moved towards each other to a second closed position or a "gripping" configuration upon simultaneous application of pressure to the first and second jaw members 12a, 12b. In the gripping configuration, the second ends 14a, 14b of the first and second jaw members 12a, 12b are biased towards each other to capture tissues therebetween during surgical procedures, such as lip biopsies.

According to an embodiment, the second end 14a of the first jaw member 12a is generally ring-shaped, including a circular wall 15 and an opening extending therethrough 17. A gripping surface of the circular wall 15 includes tissue-gripping teeth or protrusions 31 extending therefrom. The second end 14b of the second jaw member 12b includes a plate 29 and a light source housing 18 detachably connected to the plate 29. In an embodiment, the plate 29 can be generally flat and oval. In an embodiment, the light source housing 18 can include a light source such as a plurality of light-emitting diode (LED) lights 19.

According to an embodiment, the main clamp body 11 includes a threaded fastener 20 extending through the first jaw member 12a and abutting the second jaw member 12b. In an embodiment, the threaded fastener 20 can include a threaded shaft 24 and a knob 22 connected, e.g., detachably connected, to the shaft 24 at one end. An opposing end of the shaft 24 can be connected to the second jaw member 12b. In an embodiment, the threaded shaft 24 can have 40-threads-per-inch (TPI). In an embodiment, the threaded fastener 20 can achieve 180° rotation and about 0.635 mm linear travel, to facilitate precise control of the threaded fastener 20. In an embodiment, the threaded fastener 20 can have twelve discrete increment settings for reproducible pressure application.

The first and second jaw members 12a, 12b can be biased towards each other when compressed to achieve a desired clamping pressure and the threaded fastener 20 can be adjusted accordingly by twisting the knob 22 to maintain the desired clamping pressure. In this way, a precise clamping pressure can be maintained.

The threaded fastener 20 can allow for precise control of the clamping pressure. By rotating the knob 22, a surgeon can incrementally adjust the distance between the first jaw member 12a and the second jaw member 12b, thereby fine-tuning the pressure applied to the clamped tissue. This feature ensures optimal tissue retention without risking excessive compression or trauma. The threaded shaft 24 is designed with a fine pitch to allow for minute adjustments, giving surgeons a high degree of control over the applied pressure.

According to an embodiment, the main clamp body 11 can include an incremental position adjuster 26 connected to the first and second jaw members 12a, 12b. The incremental position adjuster 26 can include a bar 41 extending from one of the first jaw member 12a and second jaw member 12b. The bar 41 can include a plurality of holes 40 defined therethrough. A pin 42 extends from another one of the first and second jaw members 12a, 12b. The bar 41 is configured to releasably engage the pin 42 within any of the plurality of holes 40 to provide discrete, incremental adjustments in the position of the first and second jaw members 12a, 12b or to lock the device in specific positions. The incremental position adjuster 26 works in conjunction with the threaded fastener 20 to facilitate achieving various pressure settings or preventing unintended pressure changes during the procedure. Accordingly, the incremental position adjuster 26 adds an extra layer of precision and stability to the clamping capability of the chalazion clamp 10.

In an embodiment, the circular wall 15 can include twenty-four teeth 31 distributed at about 15° intervals around the circumference of the circular wall 15. Each of the teeth 31 can be angled inwardly, forming an angle of about 12° with respect to the wall 15. The teeth 31 can have varying heights relative to the circular wall 15. In an embodiment, the teeth can be configured with graduated teeth heights ranging from about 0.8 mm to about 1.2 mm for even pressure distribution. In an embodiment, the teeth can have textured surfaces, e.g., micro-textured surfaces, for enhanced tissue engagement, without trauma.

In an embodiment, the detachable light source housing 18 is connected to the plate 29 in a snap fit configuration. In an embodiment, the light source housing 18 can be positioned in an angle relative to the plate 29. For example, in an embodiment, the light source housing 18 can be positioned such that angle of about 15° e.g., 15°±2°, is achieved between the light source housing 18 and the tissue to be grasped by the clamp 10. In an embodiment, the housing 18 includes a waterproof seal 25 to protect electronic components of the light source. In an embodiment, the waterproof seal 25 can include an IP68-rated waterproof sealing system (water resistant in fresh water to a maximum depth of 1.5 meters for up to 30 minutes). Accordingly, the light source housing 18 can withstand autoclave sterilization.

Figure 2:
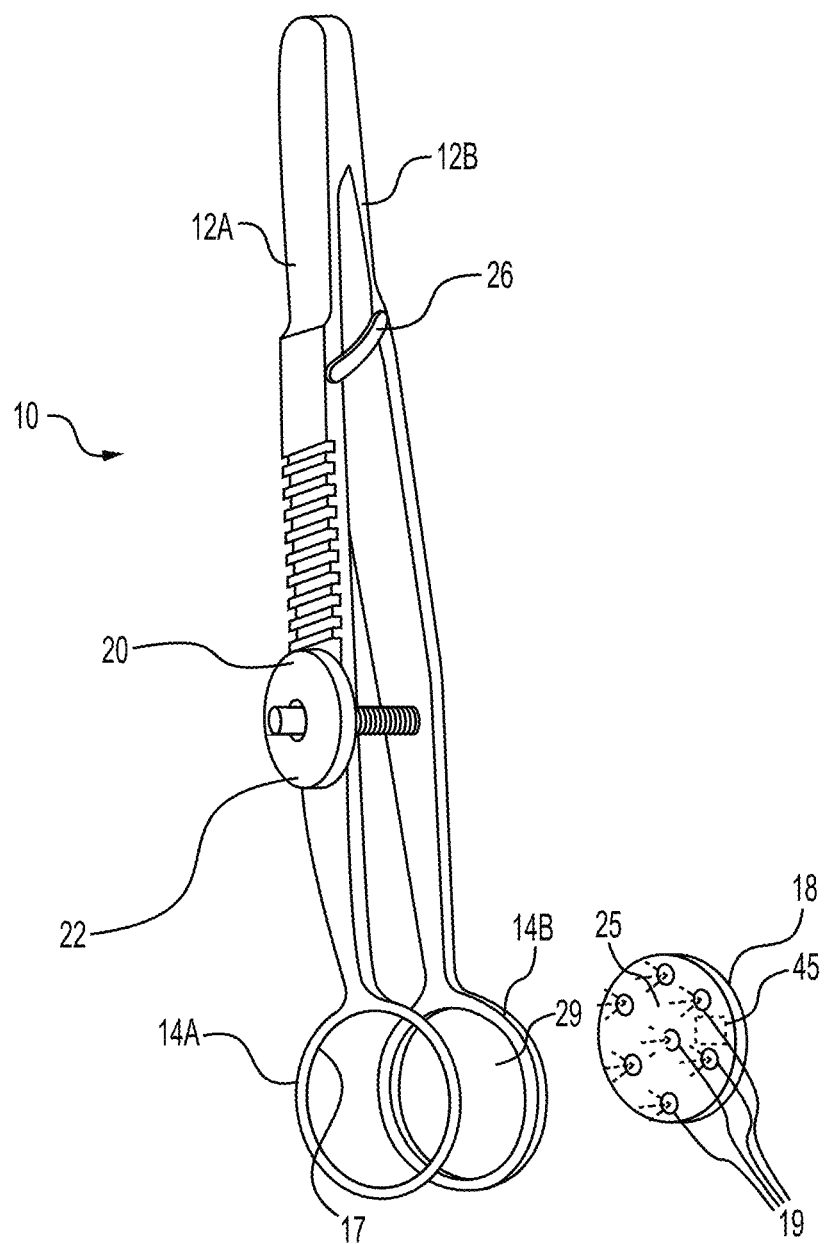
FIG. 2 is a perspective view of the chalazion clamp showing the clamp main body and the detachable light source housing separately.
Figure 3:
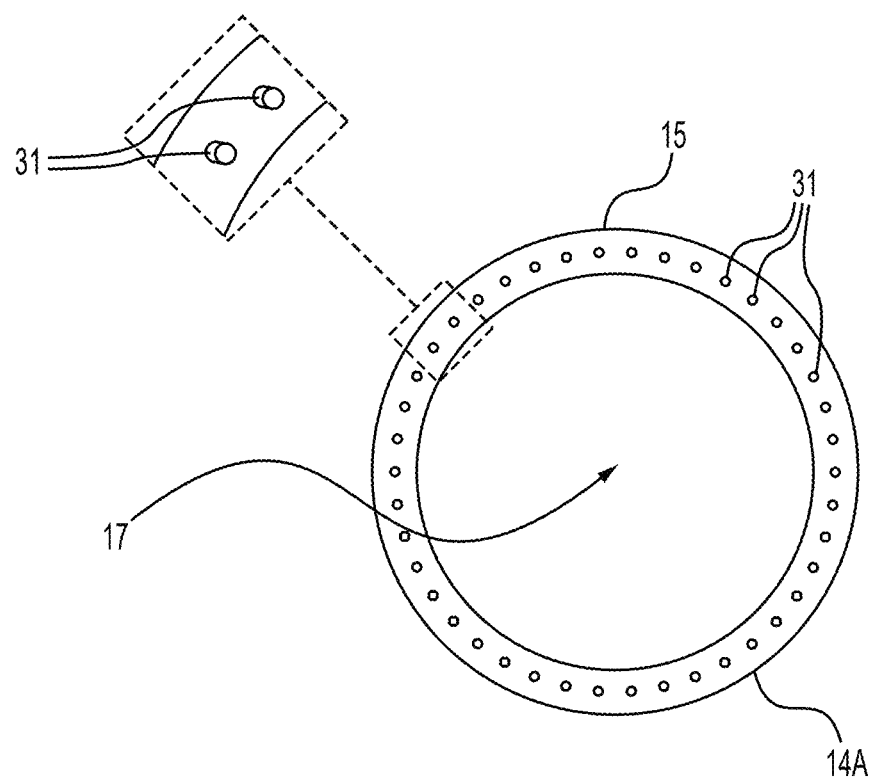
FIG. 3 shows the ring-shaped end of the first arm including the apertures defined therethrough.

In an embodiment, the housing 18 includes a rechargeable battery pack 45 (FIG. 2) for charging the light source. In an embodiment, the light source includes a plurality of LED lights 19 positioned to provide direct illumination of the target tissue, significantly enhancing visibility during surgical procedures. The LED lights 19 can be powered by the rechargeable battery pack 45 within the detachable light source housing 18. In an embodiment, a beam angle of the LED can be about 40° for precise surgical field illumination. In an embodiment, the light source provides a uniform illumination field diameter, e.g., a uniform illumination field diameter of about 2.5 cm, at optimal working distance. The light intensity can be adjustable, allowing surgeons to optimize illumination based on the specific requirements of each procedure.

The light source housing 18 can be detached from the plate 29 to facilitate sterilization. In an embodiment, the first and second jaw members 12a, 12b can be constructed from surgical-grade stainless steel, ensuring durability and allowing for repeated sterilization. As such, the first and second jaw members 12a, 12b can be corrosion resistant and capable of withstanding high-temperature sterilization processes.

The detachable light source housing 18 can be made from sterilizable, medical-grade polymers and designed to withstand standard sterilization procedures when detached from the main clamp body 11.

Prior to use, the main clamp body 11 and the detachable light source housing 18 can be sterilized separately using standard medical sterilization techniques. The sterilized light source housing 18 can then be attached to the plate 29 of the second arm 12b. In an embodiment, the housing 18 can fit securely within the plate 29, preferably in a snap fit configuration.

In use, tissue can be clamped within the jaw members 12a, 12b of the chalazion clamp 10 by positioning the tissue between the second, ring-shaped end 14a of the first jaw member 12a and the flat, oval plate 29 at the second end of the second jaw member 12b. The tissue-gripping teeth 31 on the ring-shaped end of the first arm 12a can help to securely hold the tissue in place.

In an embodiment, clamping pressure can be adjusted by rotating the circular knob 22 of the threaded fastener 20. This action moves the threaded shaft 24, which in turn adjusts the distance between the first jaw member 12a and the second jaw member 12b. The incremental adjuster 26 can be used to lock the clamp 10 at the desired pressure level, if desired.

Once the tissue is securely clamped, the light source can be activated. The light source can provide optimal illumination of the surgical site, enhancing visibility especially in areas with limited ambient light. Throughout the procedure, the tissue remains stable due to the gripping action of the tissue-gripping teeth at the ring-shaped end of the second arm and the adjustable pressure mechanism of the threaded fastener that allows the surgeon to modify the clamping force as needed.

After the procedure, the light source housing can be easily detached for separate cleaning and sterilization, allowing for thorough sterilization of both the clamp and the lighting component.

Accordingly, the chalazion clamp can provide enhanced visibility through the integrated, adjustable, and detachable light source. Additionally, the detachable light source design provides improved hygiene and sterilization capabilities. Finally, improved tissue stability is achieved with the specially designed tissue-gripping teeth, and precise control of clamping pressure via the position adjuster. As set forth herein, the chalazion clamp can provide a pre-determined light beam angle (e.g., 40°) a pre-determined light source housing angle (e.g., 15°±2°), a precisely engineered tissue stabilization system including 24 teeth at 15° intervals and a 12° inward angle, a quantifiable pressure control mechanism (40-TPI, 0.635 mm/180° travel), and advance sterilization capability. The chalazion clamp can be used in various oral surgical procedures, including lip biopsies and similar interventions. The enhanced ergonomics of the chalazion clamp can facilitate ease of use and potentially reduce surgeon fatigue during lengthy procedures.

It is to be understood that the chalazion clamp is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A chalazion clamp, comprising:
a main clamp body including
a first jaw member and a second jaw member connected together at first ends thereof and spaced apart at second ends thereof, the second end of the first jaw member having a circular wall and a central opening defined through the circular wall, and the second end of the second jaw member including a plate having a circular surface,
a plurality of gripping teeth protruding from an inner surface of the circular wall of the first jaw member, and
a threaded fastener extending through the first jaw member and abutting the second jaw member, the threaded fastener including a threaded shaft extending through the first jaw member and a knob connected to the shaft at a first end; and
a light source housing being circular and including a light source, the light source housing detachably connected directly to the circular surface of the plate.

2. The chalazion clamp of claim 1, further comprising an incremental position adjuster connected to the first and second jaw members, the incremental position adjuster including a bar extending from one of the first and second jaw members and a pin extending from another one of the first and second jaw members, the bar including a plurality of holes defined therethrough and configured to releasably engage the pin within any of the plurality of holes.

3. The clamp of claim 1, wherein the light source housing detachably engages the plate at the second end of the second jaw member.

4. The clamp of claim 1, wherein the plurality of gripping teeth have varying heights relative to the circular wall.

5. The clamp of claim 1, wherein the plurality of gripping teeth are angled inwardly toward the central opening.

6. The clamp of claim 5, wherein the gripping teeth form an angle of about 12° relative to the circular wall.

7. The clamp of claim 1, wherein the light source housing is positioned within the plate at an angle of about 15° relative to the plate.

8. The clamp of claim 1, wherein the light source comprises a plurality of LED lights.

9. The clamp of claim 8, wherein a beam angle of the plurality of LED lights is about 40° for precise surgical field illumination.

10. The clamp of claim 1, wherein the housing further comprises a waterproof seal to protect electronic components of the light source.

11. The clamp of claim 1, wherein the housing includes a rechargeable battery pack for charging the light source.

12. A chalazion clamp, comprising:
   a main clamp body including
      a first jaw member and a second jaw member connected together at first ends thereof and spaced apart at seconds thereof, the second end of the first jaw member having a circular wall and a central opening defined through the circular wall, and the second end of the second jaw member including a plate having a circular surface,
      a plurality of gripping teeth protruding from an inner surface of the circular wall of the first jaw member, and
      a threaded fastener extending through the first jaw member and abutting the second jaw member, the threaded fastener including a threaded shaft extending through the first jaw member and a knob connected to the shaft at a first end,
      an incremental position adjuster connected to the first and second jaw members, the incremental position adjuster including a bar extending from one of the first and second jaw members and a pin extending from another one of the first and second jaw members, the bar including a plurality of holes defined therethrough and configured to releasably engage the pin within any of the plurality of holes; and
   a light source housing being circular and including a light source, the light source housing detachably connected directly to the circular surface of the plate.

13. The chalazion clamp of claim 12, wherein the light source housing detachably engages the plate at the second end of the second jaw member.

14. The chalazion clamp of claim 12, wherein the light source comprises a plurality of LED lights.

15. The chalazion clamp of claim 12, wherein the housing further comprises a waterproof seal to protect electronic components of the light source.

16. The clamp of claim 12, wherein the housing includes a rechargeable battery pack for charging the light source.

* * * * *